US005501969A

United States Patent [19]
Hastings et al.

[11] Patent Number: 5,501,969
[45] Date of Patent: Mar. 26, 1996

[54] HUMAN OSTEOCLAST-DERIVED CATHEPSIN

[75] Inventors: Gregg A. Hastings, Rockville; Mark D. Adams, Potomac; Claire M. Fraser, Gueenstown; Norman H. Lee, Woodstock, all of Md.; Ewen F. Kirkness, Washington, D.C.; Judith A. Blake, Laurel; Lisa M. Fitzgerald, Germantown, both of Md.; Fred H. Drake, Glenmoore; Maxine Gowan, Valley Forge, both of Pa.

[73] Assignee: Human Genome Sciences, Inc., Rockville, Md.

[21] Appl. No.: 208,007

[22] Filed: Mar. 8, 1994

[51] Int. Cl.$^6$ .......................... C12N 15/57; C12N 15/63; C12N 1/21; C12N 5/10
[52] U.S. Cl. .................................. 435/240.2; 435/252.3; 435/254.11; 435/320.1; 536/23.2; 536/24.3
[58] Field of Search ........................ 536/23.2; 435/320.1, 435/240.2, 252.3, 219

[56] References Cited

PUBLICATIONS

Lerner, V. H. and Grubb, A., Human Cystatin C, a Cysteine Proteinase Inhibitor, Inhibits Bone Resorption In Vitro Stimulated by Parathyroid Harmone and Parathyroid Hormone Related Peptide of Malignancy, Journal of Bone and Mineral Research, 7:433–439 (1992).

Smith, S. M. and Gottesmann, M. M., Activity and Deletion Analysis of Recombinant Human Cathepsin L Expressed in *E. Coli* J. Biol. Chem., 264:20487–20495 (1989).

Bromme, D. et al., Functional Expression of Human Cathepsins in *Saccharomyces Cerevisiae*, J. Biol. Chem., 268:4832–4838 (1993).

Kane, S. E. and Gottesmann, M. M., The role of Cathepsin L in Malignant Transformation, Seminars in Cancer Biology 1:127–136 (1990).

Sloane, B. F., Cathepsin B and Cystatins: Evidence for a Role in Cancer Progression, Seminars in Cancer Biology, 1:137–152 (1990).

Delaisse, J. M., The Effects of Inhibitors of Cysteine—Proteinases and Collagenase on the Resorptive Activity of Isolated Osteoclasts Bone, 8:305–313 (1987).

Tezuka, K. et al., Molecular Cloning of a Possible Cysteine J. Biology Chem. 269:1106–1109 (1994).

Hashimoto et al., World Patent Index (WPI), Accession No. 92–317846/39 (EP 504938), 1992.

Ando et al., WPI Accession No. 93–037845/05 (EP 525420), 1993.

Ando et al., WPI Accession No. 93–001259/01 (EP520427), 1992.

Keppler et al., WPI Accession No. 91–058150/08 (WO 91/01378), 1991.

Smith et al., J. Biol. Chem. 264:20487–20495 (1989).

*Primary Examiner*—Robert A. Wax
*Assistant Examiner*—Eric Grimes
*Attorney, Agent, or Firm*—Elliot M. Olstein; Gregory D. Ferraro

[57] ABSTRACT

Disclosed is a human osteoclast-derived cathepsin (Cathepsin O) polypeptide and DNA(RNA) encoding such cathepsin O polypeptides. Also provided is a procedure for producing such polypeptide by recombinant techniques. The present invention also discloses antibodies, antagonists and inhibitors of such polypeptide which may be used to prevent the action of such polypeptide and therefore may be used therapeutically to treat bone diseases such as osteoporosis and cancers, such as tumor metastases.

39 Claims, 5 Drawing Sheets

| | | |
|---|---|---|
| 1 | TCAGATTTCCATCAGCAGGATGTGGGGGCTCAAGGTTCTGCTGCTACCTGTGGTGAGCTT | 60 |
| 1 |               M  W  G  L  K  V  L  L  L  P  V  V  S  F | 14 |
| 61 | TGCTCTGTACCCTGAGGAGATACTGGACACCCACTGGGAGCTATGGAAGAAGACCCACAG | 120 |
| 15 | A  L  Y  P  E  E  I  L  D  T  H  W  E  L  W  K  K  T  H  R | 34 |
| 121 | GAAGCAATATAACAACAAGGTGGATGAAATCTCTCGGCGTTTAATTTGGGAAAAAAACCT | 180 |
| 35 | K  Q  Y  N  N  K  V  D  E  I  S  R  R  L  I  W  E  K  N  L | 54 |
| 181 | GAAGTATATTTCCATCCATAACCTTGAGGCTTCTCTTGGTGTCCATACATATGAACTGGC | 240 |
| 55 | K  Y  I  S  I  H  N  L  E  A  S  L  G  V  H  T  Y  E  L  A | 74 |
| 241 | TATGAACCACCTGGGGGACATGACCAGTGAAGAGGTGGTTCAGAAGATGACTGGACTCAA | 300 |
| 75 | M  N  H  L  G  D  M  T  S  E  E  V  V  Q  K  M  T  G  L  K | 94 |
| 301 | AGTACCCCTGTCTCATTCCCGCAGTAATGACACCCTTTATATCCCAGAATGGGAAGGTAG | 360 |
| 95 | V  P  L  S  H  S  R  S  N  D  T  L  Y  I  P  E  W  E  G  R | 114 |
| 361 | AGCCCCAGACTCTGTCGACTATCGAAAGAAAGGATATGTTACTCCTGTCAAAAATCAGGG | 4 |
| 115 | A  P  D  S  V  D  Y  R  K  K  G  Y  V  T  P  V  K  N  Q  G | 134 |
| 421 | TCAGTGTGGTTCCTGTTGGGCTTTTAGCTCTGTGGGTGCCCTGGAGGGCCAACTCAAGAA | 480 |
| 135 | Q  C  G  S  C  W  A  F  S  S  V  G  A  L  E  G  Q  L  K  K | 154 |
| 481 | GAAAACTGGCAAACTCTTAAATCTGAGTCCCCAGAACCTAGTGGATTGTGTGTCTGAGAA | 540 |
| 155 | K  T  G  K  L  L  N  L  S  P  Q  N  L  V  D  C  V  S  E  N | 174 |
| 541 | TGATGGCTGTGGAGGGGGCTACATGACCAATGCCTTCCAATATGTGCAGAAGAACCGGGG | 600 |
| 175 | D  G  C  G  G  G  Y  M  T  N  A  F  Q  Y  V  Q  K  N  R  G | 194 |
| 601 | TATTGACTCTGAAGATGCCTACCCATATGTGGGACAGGAAGAGAGTTGTATGTACAACCC | 660 |
| 195 | I  D  S  E  D  A  Y  P  Y  V  G  Q  E  E  S  C  M  Y  N  P | 214 |
| 661 | AACAGGCAAGGCAGCTAAATGCAGAGGGTACAGAGAGATCCCCGAGGGGAATGAGAAAGC | 720 |
| 215 | T  G  K  A  A  K  C  R  G  Y  R  E  I  P  E  G  N  E  K  A | 234 |
| 721 | CCTGAAGAGGGCAGTGGCCCGAGTGGGACCTGTCTCTGTGGCCATTGATGCAAGCCTGAC | 780 |
| 235 | L  K  R  A  V  A  R  V  G  P  V  S  V  A  I  D  A  S  L  T | 254 |

FIG.1A

```
781  CTCCTTCCAGTTTTACAGCAAAGGTGTGTATTATGATGAAAGCTGCAATAGCGATAATCT  840
255   S   F   Q   F   Y   S   K   G   V   Y   Y   D   E   S   C   N   S   D   N   L    274

841  GAACCATGCGGTTTTGGCAGTGGGATATGGAATCCAGAAGGGAAACAAGCACTGGATAAT  900
275   N   H   A   V   L   A   V   G   Y   G   I   Q   K   G   N   K   H   W   I   I    294

901  TAAAAACAGCTGGGGAGAAAACTGGGGAAACAAAGGATATATCCTCATGGCTCGAAATAA  960
295   K   N   S   W   G   E   N   W   G   N   K   G   Y   I   L   M   A   R   N   K    314

961  GAACAACGCCTGTGGCATTGCCAACCTGGCCAGCTTCCCCAAGATGTGACTCCAGCCAGC  1020
315   N   N   A   C   G   I   A   N   L   A   S   F   P   K   M   *                    329

1021 CAAATCCATCCTGCTCTTCCATTTCTTCCACGATGGTGCAGTGTAACGATGCACTTTGGA  1080
1081 AGGGAGTTGGTGTGCTATTTTTGAAGCAGATGTGGTGATACTGAGATTGTCTGTTCAGTT  1140
1141 TCCCCATTTGTTTGTGCTTCAAATGATCCTTCCTACTTTGCTTCTCTCCACCCATGACCT  1200
1201 TTTTCACTGTGGCCATCAGGACTTTCCCCTGACAGCTGTGTACTCTTAGGCTAAGAGATG  1260
1261 TGACTACAGCCTGCCCCTGACTGTGTTGTCCCAGGGCTGATGCTGTACAGGTACAGGCTG  1320
1321 GAGATTTTCACATAGGTTAGATTCTCATTCACGGGACTAGTTAGCTTTAAGCACCCTAGA  1380
```

FIG. 1B

```
                    1                                                           50
        HumcatO     ........MW GLKVLLLPVV SFA.LYPEEI LDTHWELWKK THRKQYNNKV
        RabOC-2     ........MW GLKVLLLPVV SFA.LHPEEI LDTQWELWKK TYSKQYNSKV
        HumcatS     .......MKR LVCVLLVCSS AVAQLHKDPT LDHHWHLWKK TYGKQYKEKN
        HumcatL     .....MNPTL ILAAFCLGIA S.ATLTFDHS LEAQWTKWKA MHNRLY.GMN
        HumcatH     MWATLPLLCA GAWLLGVPVC GAAELSVNSL EKFHFKSWMS KHRKTYST..
        HumcatB     .......... .......... .......... ...MWQLWAS LCCLLVLANA
        HumcatD     .......MQP SSLLPLALCL LAAPASALVR IPLHKFTSIR RTMSEVGGSV
        HumcatE     .......MKT LLLLLLVLLE LGEAQGSLHR VPLRRHPSLK KKLRARSQ.L
        HumcatG     .......MQP LLLLLAFLLP TGAEAGEI.. .......... .....IGGRE 51                                                          100
        HumcatO     DEISRRL.IW EKNLKYISIH NLEASLGVHT YELAMNHLGD MTSEEVVQKM
        RabOC-2     DEISRRL.IW EKNLKHISIH NLEASLGVHT YELAMNHLGD MTSEEVVQKM
        HumcatS     EEAVRRL.IW EKNLKFVMLH NLEHSMGMHS YDLGMNHLGD MTSEEVMSLM
        HumcatL     EEGWRRA.VW EKNMKMIELH NQEYREGKHS FTMAMNAFGD MTSEEFRQVM
        HumcatH     EEYHHRLQTF ASNWRKINAH N....NGNHT FKMALNQFSD MSFAEIKHKY
        HumcatB     RSRPSFHPVS DELVNYVNKR NTTWQAGHNF YNVDMSYLKR LCGTFL....
        HumcatD     EDLIAKGPVS KYSQAVPAVT EGPIPEVLKN Y.MDAQYYGE IGIGTPPQCF
        HumcatE     SEFWKSHNLD MIQFTESCSM DQSAKEPLIN Y.LDMEYFGT ISIGSPPQNF
        HumcatG     SRPHSRPYMA YLQIQSPAGQ SRCG.....G F.LVREDFVL TAAHCWGSNI 101                                                         150
        HumcatO     TGLKVPLSHS RSNDTLYIPE WEGRAP.DSV DYRKKG.YVT PVKNQGQCGS
        RabOC-2     TGLKVPPSRS HSNDTLYIPD WEGRTP.DSI DYRKKG.YVT PVKNQGQCGS
        HumcatS     SSLRVP.SQW QRNIT.YKSN PNRILP.DSV DWREKG.CVT EVKYQGSCGA
        HumcatL     NGFQ...NRK PRKGKVFQEP LFYEAP.RSV DWREKG.YVT PVKNQGQCGS
        HumcatH     L.WSEPQNCS ATKSNYLRGT ..GPYP.PSV DWRKKGNFVS PVKNQACGS
        HumcatB     ......GGPK PPQRVMFTED LKLPASFDAR EQWPQCPTIK EIRDQGSCGS
        HumcatD     TVVFDTGSSN LWVPSIHCKL LDIACWIHHK YNSDKS..ST YVKNGTSFDI
        HumcatE     TVIFDTGSSN LWVPSVYCT. .SPACKTHSR FQPSQS..ST YSQPGQSFSI
        HumcatG     NVTLG..... .......... ...AHNIQRR ENTQQH..IT ARRAIR..HP 151                                                         200
        HumcatO     CWAFSSVGAL EGQLKKKTGK LLN..LSPQN LVDCVSE... ND..GCGGGY
        RabOC-2     CWAFSSVGAL EGQLKKKTGK LLN..LSPQN LVDCVSE... NY..GCGGGY
        HumcatS     CWAFSAVGAL EAQLKLKTGK LVS..LSAQN LVDCSTEKYG NK..GCNGGF
        HumcatL     CWAFSATGAL EGQMFRKTGR LIS..LSEQN LVDC.SGPQG NE..GCNGGL
        HumcatH     CWTFSTTGAL ESAIAIATGK MLS..LAEQQ LVDC.AQDFN NY..GCQGGL
        HumcatB     CWAFGAVEAI SDRICIHTNA HVSVEVSAED LLTCCGSMCG D...GCNGGY
        HumcatD     HYGSGSLSGY LSQDTVSVPC QSASSASALG GVKVERQVFG EATKQPGITF
        HumcatE     QYGTGSLSGI IGADQVSV.. ........E GLTVVGQQFG ESVTEPGQTF
        HumcatG     QYNQRTIQND IMLLQLSRR. .......... .VRRNRNVNP VALPRAQEGL
```

FIG.2A

```
            201                                                         250
HumcatO     MTNAFQYVQK NRGIDSEDAY .......... ............ ...PYVGQEE
RabOC-2     MTNAFQYVQR NRGIDSEDAY .......... ............ ...PYVGQDE
HumcatS     MTTAFQYIID NKGIDSDASY .......... ............ ...PYKAMDL
HumcatL     MDYAFQYVQD NGGLDSEESY .......... ............ ...PYEATEE
HumcatH     PSQAFEYILY NKGIMGEDTY .......... ............ ...PYQGKDG
HumcatB     PAEAWNF.WT RKGLVSGGLY ESHVGCRPYS IPPCEHHVNG SRPPCTGEGD
HumcatD     IAAKFDGIL. ...GMAYPRIS VNNVLPVFDN LMQQKLVDQN IFSFYLSRDP
HumcatE     VDAEFDGIL. ...GLGYPSLA VGGVTPVFDN MMAQNLVDLP MFSVYMSSNP
HumcatG     RPGTLCTVA. ...G..WGRVS MRRGTDTLRE VQLRVQRDRQ CLRIFGSYDP 251                                                         300
HumcatO     SCM....... .YNPTGKAAK CRGYREIPEG N.EKALKRAV ARVGPVSVAI
RabOC-2     SCM....... .YNPTGKAAK CRGYREIPEG N.EKALKRAV ARVGPVSVAI
HumcatS     KCQ....... .YDSKYRAAT CSKYTELPYG R.EDVLKEAV ANKGPVSVGV
HumcatL     SCK....... .YNPKYSVAN DTGFVDIPK. Q.EKALMKAV ATVGPISVAI
HumcatH     YCK....... .FQPGKAIGF VKDVANITIY D.EEAMVEAV ALYNPVSFAF
HumcatB     TPKCSKICEP GYSPTYKQDK HYGYNSYSVS NSEKDIMAEI YKNGPVEGAF
HumcatD     DAQPGGELML GGTDSKYYKG SLSYLNVTRK AYWQVHLDQV EVASGLTLCK
HumcatE     EGGAGSELIF GGYDHSHFSG SLNWVPVTKQ AYWQIALDNI QVGGTVMFCS
HumcatG     RRQ....... .......... ....ICVGDR RERKAAFK.. GDSGGPLLCN 301                                                         350
HumcatO     DASLTSFQFY SKGVYYDESC ..NSDNLNHA VLAVGYGIQ. ...KGNKHWI
RabOC-2     DASLTSFQFY SKGVYYDENC ..SSDNVNHA VLAVGYGIQ. ...KGNKHWI
HumcatS     DARHPSFFLY RSGVYYEPSC ...TQNVNHG VLVVGYGDL. ...NGKEYWL
HumcatL     DAGHESFLFY KEGIYFEPDC ..SSEDMDHG VLVVGYGFES TESDNNKYWL
HumcatH     EVTQD.FMMY RTGIYSSTSC HKTPDKVNHA VLAVGY... .EKNGIPYWI
HumcatB     SV.YSDFLLY KSGVYQHVTG EMMGG...HA IRILGWGVE. ...NGTPYWL
HumcatD     EGCEA...IV DTGTSLMVGP VDEVRELQKA IGAVPLIQGE YMIPCEKVST
HumcatE     EGCQA...IV DTGTSLITGP SDKIKQLQNA IGAAP.VDGE YAVECANLNV
HumcatG     NVAHG...IV SYGKSSGVPP ....EVFTRV SSFLPWIRTT MR....SFKL 351                                                         400
HumcatO     IK......NS WGENWGNKGY ILMARNKNNA CGIAN..LAS FPKM......
RabOC-2     IK......NS WGESWGNKGY ILMARNKNNA CGIAN..LAS FPKM......
HumcatS     VK......NS WGHNFGEEGY IRMARNKGNH CGIAS..FPS YPEI......
HumcatL     VK......NS WGEEWGMGGY VKMAKDRRNH CGIAS..AAS YPTV......
HumcatH     VK......NS WGPQWGMNGY FLIERGK.NM CGLAA..CAS YPIPLV....
HumcatB     VA......NS WNTDWGDNGF FKILRGQ.DH CGIESEVVAG IPRTDQYWEK
HumcatD     LPAITLKLGG KGYKLSPEDY TLKVSQAGKT LCLSGFMGMD IPPPSGPLWI
HumcatE     MPDVTFTING VPYTLSPTAY TLLDFVDGMQ FCSSGFQGLD IHPPAGPLWI
HumcatG     LDQMETPL.. .......... .......... .......... ..........
```

FIG.2B

```
           401           428
HumcatO  .......... .......... ........
RabOC-2  .......... .......... ........
HumcatS  .......... .......... ........
HumcatL  .......... .......... ........
HumcatH  .......... .......... ........
HumcatB  I......... .......... ........
HumcatD  LGDVFIGRYY TVFDRDNNRV GFAEAARL
HumcatE  LGDVFIRQFY SVFDRGNNRV GLAPAVP.
HumcatG  .......... .......... ........
```

FIG.2C

HUMAN OSTEOCLAST-DERIVED CATHEPSIN

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human osteoclast-derived cathepsin (Cathepsin O). The invention also relates to inhibiting the action of such polypeptide and to assays for identifying inhibitors of the polypeptide.

Bone resorption involves the simultaneous removal of both the mineral and the organic constituents of the extracellular matrix. This occurs mainly in an acidic phagolysosome-like extracellular compartment covered by the ruffled border of osteoclasts. Barron, et al., J. Cell Biol., 101:2210–22, (1985). Osteoclasts are multinucleate giant cells that play key roles in bone resorption. Attached to the bone surface, osteoclasts produce an acidic microenvironment between osteoclasts and bone matrix. In this acidic microenvironment, bone minerals and organic components are solubilized. Organic components, mainly type-I collagen, are thought to be solubilized by protease digestion. There is evidence that cystsine proteinases may play an important role in the degradation of organic components of bone. Among cystsine proteinases, cathepsins B, L, N, and S can degrade type-I collagen in the acidic condition. Etherington, D. J. Biochem. J., 127, 685–692 (1972). Cathepsin L is the most active of the lysosomal cysteine proteases with regard to its ability to hydrolyze azocasein, elastin, and collagen.

Cathepsins are proteases that function in the normal physiological as well as pathological degradation of connective tissue. Cathepsins play a major role in intracellular protein degradation and turnover, bone remodeling, and prohormone activation. Marx, J. L., Science. 235:285–286 (1987). Cathepsin B, H, L and S are ubiquitously expressed lysosomal cysteine proteinases that belong to the papain superfamily. They are found at constitutive levels in many tissues in the human including kidney, liver, lung and spleen. Some pathological roles of cathepsins include an involvement in glomerulonephritis, arthritis, and cancer metastasis. Sloan, B. F., and Honn, K. V., Cancer Metastasis Rev., 3:249–263 (1984). Greatly elevated levels of cathepsin L and B mRNA and protein are seen in tumor cells. Cathepsin L mRNA is also induced in fibroblasts treated with tumor promoting agents and growth factors. Kane, S. E. and Gottesman, M. M. Cancer Biology, 1:127–136 (1990).

In vitro studies on bone resorption have shown that cathepsins L and B may be involved in the remodelling of this tissue. These lysosomal cysteine proteases digest extracellular matrix proteins such as elastin, laminin, and type I collagen under acidic conditions. Osteoclast cells require this activity to degrade the organic matrix prior to bone regeneration accomplished by osteoblasts. Several natural and synthetic inhibitors of cysteine proteinases have been effective in inhibiting the degradation of this matrix.

The isolation of cathepsins and their role in bone resorption has been the subject of an intensive study. OC-2 has recently been isolated from pure osteoclasts from rabbit bones. The OC-2 was found to encode a possible cysteine proteinase structurally related to cathepsins L and S. Tezuka, K., et al., J. Biol. Chem., 269:1106–1109, (1994).

An inhibitor of cysteine proteinases and collagenase, Z-Phe-Ala-CHN$_2$ has been studied for its effect on the resorptive activity of isolated osteoclasts and has been found to inhibit resorption pits in dentine. Delaisse, J. M. et al., Bone, 8:305–313 (1987). Also, the effect of human recombinant cystatin C, a cysteine proteinase inhibitor, on bone resorption in vitro has been evaluated, and has been shown to significantly inhibit bone resorption which has been stimulated by parathyroid hormone. Lerner, U. H. and Grubb Anders, Journal of Bone and Mineral Research, 7:433–439, (1989). Further, a cDNA clone encoding the human cysteine protease cathepsin L has been recombinantly manufactured and expressed at high levels in E. coli in a T7 expression system. Recombinant human procathepsin L was successfully expressed at high levels and purified as both procathepsin L and active processed cathepsin L forms. Information about the possible function of the propeptide in cathepsin L folding and/or processing and about the necessity for the light chain of the enzyme for protease activity was obtained by expressing and purifying mutant enzymes carrying structural alterations in these regions. Smith, S. M. and Gottesman, M. M., J. Bio Chem., 264:20487–20495, (1989). There has also been reported the expression of a functional human cathepsin S in *Saccharomyces cerevisiae* and the characterization of the recombinant enzyme. Bromme, D. et al., J. Bio Chem., 268:4832–4838 (1993).

In accordance with one aspect of the present invention, there is provided a novel mature polypeptide which is a osteoclast-derived cathepsin as well as fragments, analogs and derivatives thereof. The human osteoclast-derived cathepsin of the present invention is of human origin.

In accordance with another aspect of the present invention, there are provided polynucleotides (DNA or RNA) which encode such polypeptides.

In accordance with still another aspect of the present invention, there is provided a procedure for producing such polypeptide by recombinant techniques.

In accordance with yet a further aspect of the present invention, there is provided an antibody which inhibits the action of such polypeptide.

In accordance with yet another aspect of the present invention, there are provided antagonists to such polypeptides, e.g., a small molecule inhibitor which may be used to inhibit the action of such polypeptide, for example, in the treatment of metastatic tumors and osteoporosis.

In accordance with still another aspect of the present invention, there is provided a procedure for developing assay systems to identify inhibitors of the polypeptide of the present invention.

These and other aspects of the present invention should be apparent to those skilled in the art from the teachings herein.

The following drawings are meant only as illustrations of specific embodiments of the present invention and are not meant as limitations in any manner.

BRIEF DESCRIPTION OF THE DRAWINGS

FIG. 1 shows the polynucleotide sequence and corresponding deduced amino acid sequence for cathepsin O. The cathepsin O shown is the predicted precursor form of the protein where approximately the first 15 amino acids represent the leader sequence and the first 115 amino acids are the prosequence. The standard three letter abbreviation has been used for the amino acid sequence.

FIG. 2 is an illustration of the amino acid homology of cathepsin O to other human cathepsins and rabbit OC-2.

In accordance with one aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75671 on Feb. 9, 1994.

A polynucleotide encoding a polypeptide of the present invention may be obtained from a cDNA library derived from human osteoclastoma cells, placenta, kidney or lung. The polynucleotide described herein was isolated from a cDNA library derived from human osteoclastoma cells. The cDNA insert is 1619 base pairs (bp) in length and contains an open reading frame encoding a protein 329 amino acids in length of which approximately the first 15 amino acids represent the leader sequence and first 115 amino acids represent the prosequence. Thus, the mature form of the polypeptide of the present invention consists of 214 amino acids after the 115 amino acid prosequence (which includes the approximately 15 amino acid leader sequence) is cleaved. The polypeptide encoded by the polynucleotide is structurally related to human cathepsin S with 56% identical amino acids and 71% similarity over the entire coding region. It is also structurally related to rabbit OC-2 cathepsin with 94% identical amino acids and 97% similarity over the entire coding region. The polypeptide may be found in lysosomes of, or extracellularly near, osteoclasts.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same, mature polypeptide as the DNA of FIG. 1 (SEQ ID NO:2) or the deposited cDNA.

The polynucleotide which encodes for the mature polypeptide of FIG. 1 (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide. The present invention also relates to polynucleotide probes constructed from the polynucleotide sequence of FIG. 1 or a segment of the sequence of FIG. 1 (SEQ ID NO:2) amplified by the PCR method, which could be utilized to screen an osteoclast cDNA library to deduce the polypeptide of the present invention.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and may in some cases be an inactive form of the protein. Once the prosequence is cleaved an active mature protein remains.

Thus, for example, the polynucleotide of the present invention may encode for a mature protein, or for a protein having a prosequence or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA.

The deposits referred to herein will be maintained under the Budapest Treaty on the International Recognition of the Deposit of Microorganisms for the purposes of Patent Procedure. These deposits are provided merely as a convenience and are not an admission that a deposit is required under 35

U.S.C. §112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to a cathepsin O polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the cathepsin O genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long as it is replicable and viable in the host.

As hereinabove indicated, the appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as E. coli, Salmonella typhimurium; Streptomyces; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, PKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well-known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Cathepsin O is recovered and purified from recombinant cell cultures by methods used heretofore, including ammonium sulfate or ethanol precipitation, acid extraction, anion or cation exchange chromatography, phosphocellulose chromatography, hydrophobic interaction chromatography, hydroxyapatite chromatography and lectin chromatography. It is preferred to have low concentrations (approximately 0.1–5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques. Pergamon Press, N.Y. (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is directed to inhibiting cathepsin O in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptide of the present invention, is used to design an antisense RNA oligonucleotide of from 10 to 40 base pairs in length. A DNA oligonucleotide is designed to be complementary to a region of the gene involved in transcription (triple helix—see Lee et al, Nucl. Acids Res., 6:3073 (1979); Cooney et al, Science, 241:456 (1988); and Dervan et al, Science, 251:1360 (1991), thereby preventing transcription and the production of cathepsin O. The antisense RNA oligonucleotide hybridizes to the mRNA in vivo and blocks translation of an mRNA molecule into the cathepsin O (antisense—Okano, J. Neurochem., 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the anti-sense RNA or DNA may be expressed in vivo to inhibit production of cathepsin O in the manner described above.

Antisense constructs to cathepsin O, therefore, inhibit the action of cathepsin O and may be used for treating certain disorders, for example, osteoporosis, since bone resorption is slowed or prevented. These antisense constructs may also be used to treat tumor metastasis since elevated levels of cathepsins are found in some tumor cells, and cathepsin L mRNA and protein is increased in ras-transformed fibroblasts. Further, there is evidence that metastatic B16 melanomas all upregulate cathepsin B compared with non-metastatic tumors.

The polypeptides, their fragments or other derivatives, or analogs thereof, or cells expressing them can be used as an immunogen to produce antibodies thereto. These antibodies can be, for example, polyclonal or monoclonal antibodies. The present also includes chimeric, single chain and humanized antibodies, as well as Fab fragments, or the product of an Fab expression library. Various procedures known in the art may be used for the production of such antibodies and fragments.

Antibodies generated against the polypeptide corresponding to a sequence of the present invention or its in vivo receptor can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Antibodies specific to the cathepsin O may further be used to inhibit the biological action of the polypeptide by binding to the polypeptide. In this manner, the antibodies may be used in therapy, for example, to treat cancer since cathepsin L mRNA and protein is increased in ras-transformed fibroblasts and after addition of phorbol esters and growth factors. Also, osteoporosis may be treated with these antibodies since bone resorption by cathepsin O is prevented.

Further, such antibodies can detect the presence or absence of cathepsin O and the level of concentration of cathepsin O and, therefore, are useful as diagnostic markers for the diagnosis of disorders such as high turnover osteoporosis, Paget's disease, tumor osteolysis, or other metabolic bone disorders. Such antibodies may also function as a diagnostic marker for tumor metastases.

The present invention is also directed to antagonists and inhibitors of the polypeptides of the present invention. The antagonists and inhibitors are those which inhibit or eliminate the function of the polypeptide.

Thus, for example, an antagonist may bind to a polypeptide of the present invention and inhibit or eliminate its function. The antagonist, for example, could be an antibody against the polypeptide which eliminates the activity of cathepsin O by binding to cathepsin O, or in some cases the antagonist may be an oligonucleotide. An example of an inhibitor is a small molecule inhibitor which inactivates the polypeptide by binding to and occupying the catalytic site, thereby making the catalytic site inaccessible to a substrate, such that the biological activity of cathepsin O is prevented. Examples of small molecule inhibitors include but are not limited to small peptides or peptide-like molecules.

In these ways, the antagonists and inhibitors may be used to treat bone disease, such as osteoporosis by preventing cathepsin O from functioning to break down bone. The antagonists and inhibitors may also be used to treat metastatic tumors since cathepsins play a role in increasing metastatic tumor growth.

The antagonists and inhibitors may be employed in a composition with a pharmaceutically acceptable carrier, including but not limited to saline, buffered saline, dextrose, water, glycerol, ethanol and combinations thereof. Administration of cathepsin inhibitors are preferably systemic. Intraperitoneal injections of the cysteine proteinase inhibitor leupeptin (0.36 mg/kg body weight) and E-64 (0.18 mg/kg body weight) in rats were able to decrease serum calcium and urinary excretion of hydroxyproline. Delaisse et al., BBRC, 125:441–447 (1984). A direct application on areas of bone vulnerable to osteoporosis such as the proximal neck of the femur may also be employed.

The present invention also relates to an assay for identifying the above-mentioned small molecule inhibitors which are specific to Cathepsin O and prevent it from functioning. Either natural protein substrates or synthetic peptides would be used to assess proteolytic activity of cathepsin O, and the ability of inhibitors to prevent this activity could be the basis for a screen to identify compounds that have therapeutic activity in disorders of excessive bone resorption. Maciewicz, R. A. and Etheringtin, D. J., BioChem. J. 256:433–440 (1988).

A general example of such an assay for identifying inhibitors of cathepsin O utilizes peptide-based substrates which are conjugated with a chromogenic tag. An illustrative example of such a peptide substrate has the $X-(Y)_n-Z$, wherein X represents an appropriate amino protecting group such as acetyl, acetate or amide, Y is any naturally or non-naturally occurring amino acid which in combination forms a substrate which cathepsin O recognizes and will cleave in the absence of an inhibitor, n represents an integer which may be any number, however, which is usually at least 20, and Z represents any chromogenic or flourogenic tag, for example, para-nitroanelide or n-methyl coumarin, which upon cleavage of the Y group by the cathepsin O can be monitored for color production. If the potential inhibitor does not inhibit cathepsin O and the substrate (Y group) is cleaved, Z has a corresponding change in configuration, which change allows fluorescence to be detected by a fluorimeter in the case of a flourogenic tag and color to be detected by a spectrophotometer in the case of a chromogenic tag. When the inhibitor successfully inhibits cathepsin O from cleaving the substrate, the Y group is not cleaved and Z does not have a change in configuration and no fluorescence or color is detectable which indicates that the inhibitor has inhibited the action of cathepsin O.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the methods of Graham, F. and Van Der Eb, A., Virology, 52:456–457 (1973).

EXAMPLE 1

Expression and Purification of the Osteoclast-derived Cathepsin

The DNA sequence encoding for cathepsin O (ATCC # 75671) is initially amplified using PCR oligonucleotide primers corresponding to the 5' and 3' end of the DNA sequence to synthesize insertion fragments. The 5' oligonucleotide primer has the sequence 5' GCTAAGGATC-CTGGGGGCTCAAGGTT 3' (SEQ ID NO:3) contains a Bam H1 restriction enzyme site followed by 15 nucleotides of cathepsin O coding sequence starting from the codon following the methionine start codon; the 3' sequence, 5' GCTAATCTAGATCACATCTTGGGGAA 3' (SEQ ID NO:4) contains complementary sequences to XbaI site, and the last 12 nucleotides of cathepsin O coding sequence. The restriction enzyme sites correspond to the restriction enzyme sites on the bacterial expression vector pQE-9 (Qiagen Inc., 9259 Eton Ave., Chatsworth, Calif. 91311). The plasmid vector encodes antibiotic resistance (Amp$^r$), a bacterial origin of replication (ori), an IPTG-regulatable promoter/operator (P/O), a ribosome binding site (RBS), a 6-histidine tag (6-His) and restriction enzyme cloning sites. The pQE-9 vector was digested with Bam HI and XbaI and the insertion fragments were then ligated into the vector maintaining the reading frame initiated at the bacterial RBS. The ligation mixture was then used to transform the E. coli strain m15/rep4 (available from Qiagen under the trademark m15/rep4). M15/rep4 contains multiple copies of the plasmid pREP4, which expresses the lacI repressor and also confers kanamycin resistance (Kan$^r$). Transformants are identified by their ability to grow on LB plates containing both Amp and Kan. Clones containing the desired constructs were grown overnight (O/N) in liquid culture in either LB media supplemented with both Amp (100 μg/ml) and Kan (25 μg/ml). The O/N culture is used to inoculate a large culture at a ratio of 1:100 to 1:250. The cells were grown to an optical density of 600 (O.D.$^{600}$) between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3–4 hours. Cells were then harvested by centrifugation. The cell pellet was solubilized in the chaotropic agent 6 molar guanidine-HCL and 50 mM NaPO$_4$ pH 8.0. After clarification, solubilized cathepsin O was purified from this solution by chromatography on a Nickel-Chelate column under conditions that allow for tight binding by proteins containing the 6-His tag. (Hochuli, E. et al., Genetic Engineering, Principle & Methods, 12:87–98 Plenum Press, New York (1990)). Cathepsin O (95% pure) was eluted from the column in 6 molar guanidine-HCL, 150 mM NaPO$_4$ pH 5.0.

EXAMPLE 2

Expression Pattern of Cathepsin O in Human Tissue

[$^{35}$S]-labeled sense or antisense riboprobes generated from a partial cDNA clone of Cathepsin O were used as part of a Northern blot analysis to probe cryosections of osteoclastoma tissue, which demonstrated a single mRNA species, and spleen tissue. Current Protocols in Molecular Biology, Vol. 2, Ausubel et al., editors, section 14.3. Total RNA was isolated from osteoclastoma tissue and spleen. The RNA was electrophoresed on a formaldehyde agarose gel, and transferred to nitrocellulose. Following pre-hybridization, the blot was hybridized overnight with either sense or antisense [32P]-labeled riboprobe at 2×106 cpm/ml at 42° C. Following stringent washes (0.2×SSC at 65° C.), the blots were exposed to x-ray film. When used in in situ hybridization on sections of osteoclastoma tissue, specific, high level expression was observed in the osteoclasts; some expression was observed in mononuclear cells, but the stromal cells and osteoblasts did not express the mRNA for Cathepsin O at detectable levels. When sections of spleen tissue were used for in situ hybridization, no expression of Cathepsin O was observed. These data indicate that the mRNA for Cathepsin O is expressed at high levels in osteoclasts, and appears to be selectively expressed in these cells.

EXAMPLE 3

Analysis of Cathepsin O Using Antibodies

Antibodies were prepared against synthetic peptides from the Cathepsin O sequence, from regions sufficiently dissimilar to other members of the cathepsin family to allow specific analysis of Cathepsin O in Western blots. The antibodies were affinity purified and used to probe Western blots of osteoclastoma tissue. Synthetic peptides (AIDASLTSFQFYSK (SEQ ID NO:5) and YDESCNS-DNLN (SEQ ID NO:6)) were prepared based upon the predicted sequence of Cathepsin O (corresponding to amino acids 248–261 and 265–275 in FIG. 1). The regions were chosen because of lowest identity to other members of the cathepsin family. The peptides were conjugated to Keyhole Limpet Hemocyanin with glutaraldehyde, mixed with adjuvant, and injected into rabbits. Immune sera was affinity purified using the immobilized peptide. Drake et al., Biochemistry, 28:8154–8160 (1989).

Tissue samples were homogenized in SDS-PAGE sample buffer and run on a 14% SDS-PAGE. The proteins were transferred to nitrocellulose, followed by blocking in bovine serum albumin. Immunoblotting was carried out with affinity purified anti-peptide antibodies, followed by alkaline phosphatase conjugated second antibody and visualization with a chromogenic substrate. Molecular mass determination was made based upon the mobility of pre-stained molecular weight standards (Rainbow markers, Amersham). Antibodies to two different peptides recognized a major band of approximately 29 kDa and a minor band of approximately 27 kDa. The immunoreactivity could be competed by the peptides used to generate the antibodies, confirming the specificity of the signal. This indicates that the mRNA for Cathepsin O is actually expressed in the tissue, and produces a protein with a size consistent with that of a fully processed Cathepsin O (assuming processing similar to related cathepsins).

Numerous modifications and variations of the present invention are possible in light of the above teachings and, therefore, within the scope of the appended claims, the invention may be practiced otherwise than as particularly described.

---

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1619 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
TCAGATTTCC  ATCAGCAGGA  TGTGGGGGCT  CAAGGTTCTG  CTGCTACCTG  TGGTGAGCTT     60
TGCTCTGTAC  CCTGAGGAGA  TACTGGACAC  CCACTGGGAG  CTATGGAAGA  AGACCCACAG    120
GAAGCAATAT  AACAACAAGG  TGGATGAAAT  CTCTCGGCGT  TTAATTTGGG  AAAAAAACCT    180
GAAGTATATT  TCCATCCATA  ACCTTGAGGC  TTCTCTTGGT  GTCCATACAT  ATGAACTGGC    240
TATGAACCAC  CTGGGGGACA  TGACCAGTGA  AGAGGTGGTT  CAGAAGATGA  CTGGACTCAA    300
AGTACCCCTG  TCTCATTCCC  GCAGTAATGA  CACCCTTTAT  ATCCCAGAAT  GGGAAGGTAG    360
AGCCCCAGAC  TCTGTCGACT  ATCGAAAGAA  AGGATATGTT  ACTCCTGTCA  AAAATCAGGG    420
TCAGTGTGGT  TCCTGTTGGG  CTTTTAGCTC  TGTGGGTGCC  CTGGAGGGCC  AACTCAAGAA    480
GAAAACTGGC  AAACTCTTAA  ATCTGAGTCC  CCAGAACCTA  GTGGATTGTG  TGTCTGAGAA    540
TGATGGCTGT  GGAGGGGGCT  ACATGACCAA  TGCCTTCCAA  TATGTGCAGA  AGAACCGGGG    600
TATTGACTCT  GAAGATGCCT  ACCCATATGT  GGGACAGGAA  GAGAGTTGTA  TGTACAACCC    660
AACAGGCAAG  GCAGCTAAAT  GCAGAGGGTA  CAGAGAGATC  CCCGAGGGGA  ATGAGAAAGC    720
CCTGAAGAGG  GCAGTGGCCC  GAGTGGGACC  TGTCTCTGTG  GCCATTGATG  CAAGCCTGAC    780
CTCCTTCCAG  TTTTACAGCA  AAGGTGTGTA  TTATGATGAA  AGCTGCAATA  GCGATAATCT    840
GAACCATGCG  GTTTTGGCAG  TGGGATATGG  AATCCAGAAG  GGAAACAAGC  ACTGGATAAT    900
TAAAAACAGC  TGGGGAGAAA  ACTGGGGAAA  CAAAGGATAT  ATCCTCATGG  CTCGAAATAA    960
GAACAACGCC  TGTGGCATTG  CCAACCTGGC  CAGCTTCCCC  AAGATGTGAC  TCCAGCCAGC   1020
CAAATCCATC  CTGCTCTTCC  ATTTCTTCCA  CGATGGTGCA  GTGTAACGAT  GCACTTTGGA   1080
AGGGAGTTGG  TGTGCTATTT  TTGAAGCAGA  TGTGGTGATA  CTGAGATTGT  CTGTTCAGTT   1140
TCCCCATTTG  TTTGTGCTTC  AAATGATCCT  TCCTACTTTG  CTTCTCTCCA  CCCATGACCT   1200
TTTTCACTGT  GGCCATCAGG  ACTTTCCCCT  GACAGCTGTG  TACTCTTAGG  CTAAGAGATG   1260
TGACTACAGC  CTGCCCCTGA  CTGTGTTGTC  CCAGGGCTGA  TGCTGTACAG  GTACAGGCTG   1320
GAGATTTTCA  CATAGGTTAG  ATTCTCATTC  ACGGGACTAG  TTAGCTTTAA  GCACCCTAGA   1380
GGACTAGGGT  AATCTGACTT  CTCACTTCCT  AAGTTCCCTT  CTATATCCTC  AAGGTAGAAA   1440
TGTCTATGTT  TTCTACTCCA  ATTCATAAAT  CTATTCATAA  GTCTTTGGTA  CAAGTTTACA   1500
TGATAAAAAG  AAATGTGATT  TGTCTTCCCT  TCTTTGCACT  TTTGAAATAA  AGTATTTATC   1560
TCCTGTCTAC  AGTTTAATAA  ATAGCATCTA  GTACACATTC  AAAAAAAAA   AAAAAAAA    1619
```

( 2 ) INFORMATION FOR SEQ ID NO:2:

( i ) SEQUENCE CHARACTERISTICS:

(A) LENGTH: 329 AMINO ACIDS
(B) TYPE: AMINO ACID
(C) STRANDEDNESS:
(D) TOPOLOGY: LINEAR (ii) MOLECULE TYPE: PROTEIN (xi) SEQUENCE DESCRIPTION: SEQ ID NO:2:

| Met | Trp | Gly | Leu | Lys | Val | Leu | Leu | Leu | Pro | Val | Val | Ser | Phe | Ala |
|---|---|---|---|---|---|---|---|---|---|---|---|---|---|---|
| -115 | | | | | -110 | | | | | -105 | | | | |
| Leu | Tyr | Pro | Glu | Glu | Ile | Leu | Asp | Thr | His | Trp | Glu | Leu | Trp | Lys |
| -100 | | | | | -95 | | | | | -90 | | | | |
| Lys | Thr | His | Arg | Lys | Gln | Tyr | Asn | Asn | Lys | Val | Asp | Glu | Ile | Ser |
| -85 | | | | | -80 | | | | | -75 | | | | |
| Arg | Arg | Leu | Ile | Trp | Glu | Lys | Asn | Leu | Lys | Tyr | Ile | Ser | Ile | His |
| -70 | | | | | -65 | | | | | -60 | | | | |
| Asn | Leu | Glu | Ala | Ser | Leu | Gly | Val | His | Thr | Tyr | Glu | Leu | Ala | Met |
| -55 | | | | | -50 | | | | | -45 | | | | |
| Asn | His | Leu | Gly | Asp | Met | Thr | Ser | Glu | Glu | Val | Val | Gln | Lys | Met |
| -40 | | | | | -35 | | | | | -30 | | | | |
| Thr | Gly | Leu | Lys | Val | Pro | Leu | Ser | His | Ser | Arg | Ser | Asn | Asp | Thr |
| -25 | | | | | -20 | | | | | -15 | | | | |
| Leu | Tyr | Ile | Pro | Glu | Trp | Glu | Gly | Arg | Ala | Pro | Asp | Ser | Val | Asp |
| -10 | | | | | -5 | | | | | 1 | | | | 5 |
| Tyr | Arg | Lys | Lys | Gly | Tyr | Val | Thr | Pro | Val | Lys | Asn | Gln | Gly | Gln |
| 10 | | | | | 15 | | | | | 20 | | | | |
| Cys | Gly | Ser | Cys | Trp | Ala | Phe | Ser | Ser | Val | Gly | Ala | Leu | Glu | Gly |
| 25 | | | | | 30 | | | | | 35 | | | | |
| Gln | Leu | Lys | Lys | Lys | Thr | Gly | Lys | Leu | Leu | Asn | Leu | Ser | Pro | Gln |
| 40 | | | | | 45 | | | | | 50 | | | | |
| Asn | Leu | Val | Asp | Cys | Val | Ser | Glu | Asn | Asp | Gly | Cys | Gly | Gly | Gly |
| 55 | | | | | 60 | | | | | 65 | | | | |
| Tyr | Met | Thr | Asn | Ala | Phe | Gln | Tyr | Val | Gln | Lys | Asn | Arg | Gly | Ile |
| 70 | | | | | 75 | | | | | 80 | | | | |
| Asp | Ser | Glu | Asp | Ala | Tyr | Pro | Tyr | Val | Gly | Gln | Glu | Glu | Ser | Cys |
| 85 | | | | | 90 | | | | | 95 | | | | |
| Met | Tyr | Asn | Pro | Thr | Gly | Lys | Ala | Ala | Lys | Cys | Arg | Gly | Tyr | Arg |
| 100 | | | | | 105 | | | | | 110 | | | | |
| Glu | Ile | Pro | Glu | Gly | Asn | Glu | Lys | Ala | Leu | Lys | Arg | Ala | Val | Ala |
| 115 | | | | | 120 | | | | | 125 | | | | |
| Arg | Val | Gly | Pro | Val | Ser | Val | Ala | Ile | Asp | Ala | Ser | Leu | Thr | Ser |
| 130 | | | | | 135 | | | | | 140 | | | | |
| Phe | Gln | Phe | Tyr | Ser | Lys | Gly | Val | Tyr | Tyr | Asp | Glu | Ser | Cys | Asn |
| 145 | | | | | 150 | | | | | 155 | | | | |
| Ser | Asp | Asn | Leu | Asn | His | Ala | Val | Leu | Ala | Val | Gly | Tyr | Gly | Ile |
| 160 | | | | | 165 | | | | | 170 | | | | |
| Gln | Lys | Gly | Asn | Lys | His | Trp | Ile | Ile | Lys | Gln | Ser | Trp | Gly | Glu |
| 175 | | | | | 180 | | | | | 185 | | | | |
| Asn | Trp | Gly | Asn | Lys | Gly | Tyr | Ile | Leu | Met | Ala | Arg | Asn | Lys | Asn |
| 190 | | | | | 195 | | | | | 200 | | | | |
| Asn | Ala | Cys | Gly | Ile | Ala | Asn | Leu | Ala | Ser | Phe | Pro | Lys | Met | |
| 205 | | | | | 210 | | | | | | | | | |

(2) INFORMATION FOR SEQ ID NO:3:

(i) SEQUENCE CHARACTERISTICS:
(A) LENGTH: 26 BASE PAIRS ( B ) TYPE: NUCLEIC ACID
( C ) STRANDEDNESS: SINGLE
( D ) TOPOLOGY: LINEAR ( i i ) MOLECULE TYPE: Oligonucleotide ( x i ) SEQUENCE DESCRIPTION: SEQ ID NO:3:

GCTAAGGATC CTGGGGGCTC AAGGTT 26

( 2 ) INFORMATION FOR SEQ ID NO:4:

( i ) SEQUENCE CHARACTERISTICS:
( A ) LENGTH: 26 BASE PAIRS
( B ) TYPE: NUCLEIC ACID
( C ) STRANDEDNESS: SINGLE
( D ) TOPOLOGY: LINEAR ( i i ) MOLECULE TYPE: Oligonucleotide ( x i ) SEQUENCE DESCRIPTION: SEQ ID NO:4:

GCTAATCTAG ATCACATCTT GGGGAA 26

( 2 ) INFORMATION FOR SEQ ID NO:5:

( i ) SEQUENCE CHARACTERISTICS:
( A ) LENGTH: 14 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:5:

Ala Ile Asp Ala Ser Leu Thr Ser Phe Gln Phe Tyr Ser Lys
                  5                  10

( 2 ) INFORMATION FOR SEQ ID NO:6:

( i ) SEQUENCE CHARACTERISTICS:
( A ) LENGTH: 11 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:6:

Tyr Asp Glu Ser Cys Asn Ser Asp Asn Leu Asn
                  5                  10

( 2 ) INFORMATION FOR SEQ ID NO:7:

( i ) SEQUENCE CHARACTERISTICS:
( A ) LENGTH: 329 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:7:

Met Trp Gly Leu Lys Val Leu Leu Leu Pro Val Val Ser Phe Ala
                  5                  10                  15

Leu His Pro Glu Glu Ile Leu Asp Thr Gln Trp Glu Leu Trp Lys
                 20                  25                  30

Lys Thr Tyr Ser Lys Gln Tyr Asn Ser Lys Val Asp Glu Ile Ser
                 35                  40                  45

Arg Arg Leu Ile Trp Glu Lys Asn Leu Lys His Ile Ser Ile His

```
                       50                         55                         60
Asn  Leu  Glu  Ala  Ser  Leu  Gly  Val  His  Thr  Tyr  Glu  Leu  Ala  Met
                       65                         70                         75

Asn  His  Leu  Gly  Asp  Met  Thr  Ser  Glu  Glu  Val  Val  Gln  Lys  Met
                       80                         85                         90

Thr  Gly  Leu  Lys  Val  Pro  Pro  Ser  Arg  Ser  His  Ser  Asn  Asp  Thr
                       95                        100                        105

Leu  Tyr  Ile  Pro  Asp  Trp  Glu  Gly  Arg  Thr  Pro  Asp  Ser  Ile  Asp
                      110                        115                        120

Tyr  Arg  Lys  Lys  Gly  Tyr  Val  Thr  Pro  Val  Lys  Asn  Gln  Gly  Gln
                      125                        130                        135

Cys  Gly  Ser  Cys  Trp  Ala  Phe  Ser  Ser  Val  Gly  Ala  Leu  Glu  Gly
                      140                        145                        150

Gln  Leu  Lys  Lys  Lys  Thr  Gly  Lys  Leu  Leu  Asn  Leu  Ser  Pro  Gln
                      155                        160                        165

Asn  Leu  Val  Asp  Cys  Val  Ser  Glu  Asn  Tyr  Gly  Cys  Gly  Gly  Gly
                      170                        175                        180

Tyr  Met  Thr  Asn  Ala  Phe  Gln  Tyr  Val  Gln  Arg  Asn  Arg  Gly  Ile
                      185                        190                        195

Asp  Ser  Glu  Asp  Ala  Tyr  Pro  Tyr  Val  Gly  Gln  Asp  Glu  Ser  Cys
                      200                        205                        210

Met  Tyr  Asn  Pro  Thr  Gly  Lys  Ala  Ala  Lys  Cys  Arg  Gly  Tyr  Arg
                      215                        220                        225

Glu  Ile  Pro  Glu  Gly  Asn  Glu  Lys  Ala  Leu  Lys  Arg  Ala  Val  Ala
                      230                        235                        240

Arg  Val  Gly  Pro  Val  Ser  Val  Ala  Ile  Asp  Ala  Ser  Leu  Thr  Ser
                      245                        250                        255

Phe  Gln  Phe  Tyr  Ser  Lys  Gly  Val  Tyr  Tyr  Asp  Glu  Asn  Cys  Ser
                      260                        265                        270

Ser  Asp  Asn  Val  Asn  His  Ala  Val  Leu  Ala  Val  Gly  Tyr  Gly  Ile
                      275                        280                        285

Gln  Lys  Gly  Asn  Lys  His  Trp  Ile  Ile  Lys  Asn  Ser  Trp  Gly  Glu
                      290                        295                        300

Ser  Trp  Gly  Asn  Lys  Gly  Tyr  Ile  Leu  Met  Ala  Arg  Asn  Lys  Asn
                      305                        310                        315

Asn  Ala  Cys  Gly  Ile  Ala  Asn  Leu  Ala  Ser  Phe  Pro  Lys  Met
                      320                        325
```

( 2 ) INFORMATION FOR SEQ ID NO:8:

( i ) SEQUENCE CHARACTERISTICS:
        ( A ) LENGTH: 331 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:8:

```
Met  Lys  Arg  Leu  Val  Cys  Val  Leu  Leu  Val  Cys  Ser  Ser  Ala  Val
                       5                          10                         15

Ala  Gln  Leu  His  Lys  Asp  Pro  Thr  Leu  Asp  His  His  Trp  His  Leu
                       20                         25                         30

Trp  Lys  Lys  Thr  Tyr  Gly  Lys  Gln  Tyr  Lys  Glu  Lys  Asn  Glu  Glu
                       35                         40                         45

Ala  Val  Arg  Arg  Leu  Ile  Trp  Glu  Lys  Asn  Leu  Lys  Phe  Val  Met
                       50                         55                         60
```

| | | | | | | | | | | | | | | |
|---|---|---|---|---|---|---|---|---|---|---|---|---|---|---|
|Leu|His|Asn|Leu|Glu<br>65|His|Ser|Met|Gly|Met<br>70|His|Ser|Tyr|Asp|Leu<br>75|
|Gly|Met|Asn|His|Leu<br>80|Gly|Asp|Met|Thr|Ser<br>85|Glu|Glu|Val|Met|Ser<br>90|
|Leu|Met|Ser|Ser|Leu<br>95|Arg|Val|Pro|Ser|Gln<br>100|Trp|Gln|Arg|Asn|Ile<br>105|
|Thr|Tyr|Lys|Ser|Asn<br>110|Pro|Asn|Arg|Ile|Leu<br>115|Pro|Asp|Ser|Val|Asp<br>120|
|Trp|Arg|Glu|Lys|Gly<br>125|Cys|Val|Thr|Glu|Val<br>130|Lys|Tyr|Gln|Gly|Ser<br>135|
|Cys|Gly|Ala|Cys|Trp<br>140|Ala|Phe|Ser|Ala|Val<br>145|Gly|Ala|Leu|Glu|Ala<br>150|
|Gln|Leu|Lys|Leu|Lys<br>155|Thr|Gly|Lys|Leu|Val<br>160|Ser|Leu|Ser|Ala|Gln<br>165|
|Asn|Leu|Val|Asp|Cys<br>170|Ser|Thr|Glu|Lys|Tyr<br>175|Gly|Asn|Lys|Gly|Cys<br>180|
|Asn|Gly|Gly|Phe|Met<br>185|Thr|Thr|Ala|Phe|Gln<br>190|Tyr|Ile|Ile|Asp|Asn<br>195|
|Lys|Gly|Ile|Asp|Ser<br>200|Asp|Ala|Ser|Tyr|Pro<br>205|Tyr|Lys|Ala|Met|Asp<br>210|
|Leu|Lys|Cys|Gln|Tyr<br>215|Asp|Ser|Lys|Tyr|Arg<br>220|Ala|Ala|Thr|Cys|Ser<br>225|
|Lys|Tyr|Thr|Glu|Leu<br>230|Pro|Tyr|Gly|Arg|Glu<br>235|Asp|Val|Leu|Lys|Glu<br>240|
|Ala|Val|Ala|Asn|Lys<br>245|Gly|Pro|Val|Ser|Val<br>250|Gly|Val|Asp|Ala|Arg<br>255|
|His|Pro|Ser|Phe|Phe<br>260|Leu|Tyr|Arg|Ser|Gly<br>265|Val|Tyr|Tyr|Glu|Pro<br>270|
|Ser|Cys|Thr|Gln|Asn<br>275|Val|Asn|His|Gly|Val<br>280|Leu|Val|Val|Gly|Tyr<br>285|
|Gly|Asp|Leu|Asn|Gly<br>290|Lys|Glu|Tyr|Trp|Leu<br>295|Val|Lys|Asn|Ser|Trp<br>300|
|Gly|His|Asn|Phe|Gly<br>305|Glu|Glu|Gly|Tyr|Ile<br>310|Arg|Met|Ala|Arg|Asn<br>315|
|Lys|Gly|Asn|His|Cys<br>320|Gly|Ile|Ala|Ser|Phe<br>325|Pro|Ser|Tyr|Pro|Glu<br>330|
|Ile| | | | | | | | | | | | | | |

( 2 ) INFORMATION FOR SEQ ID NO:9:

( i ) SEQUENCE CHARACTERISTICS:
        ( A ) LENGTH: 333 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:9:

| | | | | | | | | | | | | | | |
|---|---|---|---|---|---|---|---|---|---|---|---|---|---|---|
|Met|Asn|Pro|Thr|Leu<br>5|Ile|Leu|Ala|Ala|Phe<br>10|Cys|Leu|Gly|Ile|Ala<br>15|
|Ser|Ala|Thr|Leu|Thr<br>20|Phe|Asp|His|Ser|Leu<br>25|Glu|Ala|Gln|Trp|Thr<br>30|
|Lys|Trp|Lys|Ala|Met<br>35|His|Asn|Arg|Leu|Tyr<br>40|Gly|Met|Asn|Glu|Glu<br>45|
|Gly|Trp|Arg|Arg|Ala|Val|Trp|Glu|Lys|Asn|Met|Lys|Met|Ile|Glu|

|  |  |  | 50 |  |  |  |  | 55 |  |  |  |  | 60 |
|--|--|--|--|--|--|--|--|--|--|--|--|--|--|

Leu His Asn Gln Glu Tyr Arg Glu Gly Lys His Ser Phe Thr Met
                    65                    70                    75

Ala Met Asn Ala Phe Gly Asp Met Thr Ser Glu Glu Phe Arg Gln
                    80                    85                    90

Val Met Asn Gly Phe Gln Asn Arg Lys Pro Arg Lys Gly Lys Val
                    95                   100                   105

Phe Gln Glu Pro Leu Phe Tyr Glu Ala Pro Arg Ser Val Asp Trp
                   110                   115                   120

Arg Glu Lys Gly Tyr Val Thr Pro Val Lys Asn Gln Gly Gln Cys
                   125                   130                   135

Gly Ser Cys Trp Ala Phe Ser Ala Thr Gly Ala Leu Glu Gly Gln
                   140                   145                   150

Met Phe Arg Lys Thr Gly Arg Leu Ile Ser Leu Ser Glu Gln Asn
                   155                   160                   165

Leu Val Asp Cys Ser Gly Pro Gln Gly Asn Glu Gly Cys Asn Gly
                   170                   175                   180

Gly Leu Met Asp Tyr Ala Phe Gln Tyr Val Gln Asp Asn Gly Gly
                   185                   190                   195

Leu Asp Ser Glu Glu Ser Tyr Pro Tyr Glu Ala Thr Glu Glu Ser
                   200                   205                   210

Cys Lys Tyr Asn Pro Lys Tyr Ser Val Ala Asn Asp Thr Gly Phe
                   215                   220                   225

Val Asp Ile Pro Lys Gln Glu Lys Ala Leu Met Lys Ala Val Ala
                   230                   235                   240

Thr Val Gly Pro Ile Ser Val Ala Ile Asp Ala Gly His Glu Ser
                   245                   250                   255

Phe Leu Phe Tyr Lys Glu Gly Ile Tyr Phe Glu Pro Asp Cys Ser
                   260                   265                   270

Ser Glu Asp Met Asp His Gly Val Leu Val Val Gly Tyr Gly Phe
                   275                   280                   285

Glu Ser Thr Glu Ser Asp Asn Asn Lys Tyr Trp Leu Val Lys Asn
                   290                   295                   300

Ser Trp Gly Glu Glu Trp Gly Met Gly Gly Tyr Val Lys Met Ala
                   305                   310                   315

Lys Asp Arg Arg Asn His Cys Gly Ile Ala Ser Ala Ala Ser Tyr
                   320                   325                   330

Pro Thr Val ( 2 ) INFORMATION FOR SEQ ID NO:10:

( i ) SEQUENCE CHARACTERISTICS:
        ( A ) LENGTH: 335 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:10:

Met Trp Ala Thr Leu Pro Leu Leu Cys Ala Gly Ala Trp Leu Leu
                    5                    10                    15

Gly Val Pro Val Cys Gly Ala Ala Glu Leu Ser Val Asn Ser Leu
                   20                    25                    30

Glu Lys Phe His Phe Lys Ser Trp Met Ser Lys His Arg Lys Thr
                   35                    40                    45

```
Tyr Ser Thr Glu Glu Tyr His His Arg Leu Gln Thr Phe Ala Ser
             50                  55                  60

Asn Trp Arg Lys Ile Asn Ala His Asn Asn Gly Asn His Thr Phe
             65                  70                  75

Lys Met Ala Leu Asn Gln Phe Ser Asp Met Ser Phe Ala Glu Ile
             80                  85                  90

Lys His Lys Tyr Leu Trp Ser Glu Pro Gln Asn Cys Ser Ala Thr
             95                 100                 105

Lys Ser Asn Tyr Leu Arg Gly Thr Gly Pro Tyr Pro Pro Ser Val
            110                 115                 120

Asp Trp Arg Lys Lys Gly Asn Phe Val Ser Pro Val Lys Asn Gln
            125                 130                 135

Gly Ala Cys Gly Ser Cys Trp Thr Phe Ser Thr Thr Gly Ala Leu
            140                 145                 150

Glu Ser Ala Ile Ala Ile Ala Thr Gly Lys Met Leu Ser Leu Ala
            155                 160                 165

Glu Gln Gln Leu Val Asp Cys Ala Gln Asp Phe Asn Asn Tyr Gly
            170                 175                 180

Cys Gln Gly Gly Leu Pro Ser Gln Ala Phe Glu Tyr Ile Leu Tyr
            185                 190                 195

Asn Lys Gly Ile Met Gly Glu Asp Thr Tyr Pro Tyr Gln Gly Lys
            200                 205                 210

Asp Gly Tyr Cys Lys Phe Gln Pro Gly Lys Ala Ile Gly Phe Val
            215                 220                 225

Lys Asp Val Ala Asn Ile Thr Ile Tyr Asp Glu Glu Ala Met Val
            230                 235                 240

Glu Ala Val Ala Leu Tyr Asn Pro Val Ser Phe Ala Phe Glu Val
            245                 250                 255

Thr Gln Asp Phe Met Met Tyr Arg Thr Gly Ile Tyr Ser Ser Thr
            260                 265                 270

Ser Cys His Lys Thr Pro Asp Lys Val Asn His Ala Val Leu Ala
            275                 280                 285

Val Gly Tyr Gly Glu Lys Asn Gly Ile Pro Tyr Trp Ile Val Lys
            290                 295                 300

Asn Ser Trp Gly Pro Gln Trp Gly Met Asn Gly Tyr Phe Leu Ile
            305                 310                 315

Glu Arg Gly Lys Asn Met Cys Gly Leu Ala Ala Cys Ala Ser Tyr
            320                 325                 330

Pro Ile Pro Leu Val
            335
```

( 2 ) INFORMATION FOR SEQ ID NO:11:

( i ) SEQUENCE CHARACTERISTICS:
        ( A ) LENGTH: 339 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:11:

```
Met Trp Gln Leu Trp Ala Ser Leu Cys Cys Leu Leu Val Leu Ala
              5                  10                  15

Asn Ala Arg Ser Arg Pro Ser Phe His Pro Val Ser Asp Glu Leu
             20                  25                  30

Val Asn Tyr Val Asn Lys Arg Asn Thr Thr Trp Gln Ala Gly His
```

```
                         35                          40                          45
Asn  Phe  Tyr  Asn  Val  Asp  Met  Ser  Tyr  Leu  Lys  Arg  Leu  Cys  Gly
                    50                       55                          60

Thr  Phe  Leu  Gly  Gly  Pro  Lys  Pro  Pro  Gln  Arg  Val  Asn  Phe  Thr
                    65                       70                          75

Glu  Asp  Leu  Lys  Leu  Pro  Ala  Ser  Phe  Asp  Ala  Arg  Glu  Gln  Trp
                    80                       85                          90

Pro  Gln  Cys  Pro  Thr  Ile  Lys  Glu  Ile  Arg  Asp  Gln  Gly  Ser  Cys
                    95                      100                         105

Gly  Ser  Cys  Trp  Ala  Phe  Gly  Ala  Val  Glu  Ala  Ile  Ser  Asp  Arg
                   110                      115                         120

Ile  Cys  Ile  His  Thr  Asn  Ala  His  Val  Ser  Val  Glu  Val  Ser  Ala
                   125                      130                         135

Glu  Asp  Leu  Leu  Thr  Cys  Cys  Gly  Ser  Met  Cys  Gly  Asp  Gly  Cys
                   140                      145                         150

Asn  Gly  Gly  Tyr  Pro  Ala  Glu  Ala  Trp  Asn  Phe  Trp  Thr  Arg  Lys
                   155                      160                         165

Gly  Leu  Val  Ser  Gly  Gly  Leu  Tyr  Glu  Ser  His  Val  Gly  Cys  Arg
                   170                      175                         180

Pro  Tyr  Ser  Ile  Pro  Pro  Cys  Glu  His  His  Val  Asn  Gly  Ser  Arg
                   185                      190                         195

Pro  Pro  Cys  Thr  Gly  Glu  Gly  Asp  Thr  Pro  Lys  Cys  Ser  Lys  Ile
                   200                      205                         210

Cys  Glu  Pro  Gly  Tyr  Ser  Pro  Thr  Tyr  Lys  Gln  Asp  Lys  His  Tyr
                   215                      220                         225

Gly  Tyr  Asn  Ser  Tyr  Ser  Val  Ser  Asn  Ser  Glu  Lys  Asp  Ile  Met
                   230                      235                         240

Ala  Glu  Ile  Tyr  Lys  Asn  Gly  Pro  Val  Glu  Gly  Ala  Phe  Ser  Val
                   245                      250                         255

Tyr  Ser  Asp  Phe  Leu  Leu  Tyr  Lys  Ser  Gly  Val  Tyr  Gln  His  Val
                   260                      265                         270

Thr  Gly  Glu  Met  Met  Gly  Gly  His  Ala  Ile  Arg  Ile  Leu  Gly  Trp
                   275                      280                         285

Gly  Val  Glu  Asn  Gly  Thr  Pro  Tyr  Trp  Leu  Val  Ala  Asn  Ser  Trp
                   290                      295                         300

Asn  Thr  Asp  Trp  Gly  Asp  Asn  Gly  Phe  Phe  Lys  Ile  Leu  Arg  Gly
                   305                      310                         315

Gln  Asp  His  Cys  Gly  Ile  Glu  Ser  Glu  Val  Val  Ala  Gly  Ile  Pro
                   320                      325                         330

Arg  Thr  Asp  Gln  Tyr  Trp  Glu  Lys  Ile
                   335
```

( 2 ) INFORMATION FOR SEQ ID NO:12:

( i ) SEQUENCE CHARACTERISTICS:
        ( A ) LENGTH: 412 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:12:

```
Met  Gln  Pro  Ser  Ser  Leu  Leu  Pro  Leu  Ala  Leu  Cys  Leu  Leu  Ala
                    5                       10                          15

Ala  Pro  Ala  Ser  Ala  Leu  Val  Arg  Ile  Pro  Leu  His  Lys  Phe  Thr
                   20                       25                          30
```

| | | | | | | | | | | | | | | |
|---|---|---|---|---|---|---|---|---|---|---|---|---|---|---|
| Ser | Ile | Arg | Arg | Thr 35 | Met | Ser | Glu | Val | Gly 40 | Gly | Ser | Val | Glu | Asp 45 |
| Leu | Ile | Ala | Lys | Gly 50 | Pro | Val | Ser | Lys | Tyr 55 | Ser | Gln | Ala | Val | Pro 60 |
| Ala | Val | Thr | Glu | Gly 65 | Pro | Ile | Pro | Glu | Val 70 | Leu | Lys | Asn | Tyr | Met 75 |
| Asp | Ala | Gln | Tyr | Tyr 80 | Gly | Glu | Ile | Gly | Ile 85 | Gly | Thr | Pro | Pro | Gln 90 |
| Cys | Phe | Thr | Val | Val 95 | Phe | Asp | Thr | Gly | Ser 100 | Ser | Asn | Leu | Trp | Val 105 |
| Pro | Ser | Ile | His | Cys 110 | Lys | Leu | Leu | Asp | Ile 115 | Ala | Cys | Trp | Ile | His 120 |
| His | Lys | Tyr | Asn | Ser 125 | Asp | Lys | Ser | Ser | Thr 130 | Tyr | Val | Lys | Asn | Gly 135 |
| Thr | Ser | Phe | Asp | Ile 140 | His | Tyr | Gly | Ser | Gly 145 | Ser | Leu | Ser | Gly | Tyr 150 |
| Leu | Ser | Gln | Asp | Thr 155 | Val | Ser | Val | Pro | Cys 160 | Gln | Ser | Ala | Ser | Ser 165 |
| Ala | Ser | Ala | Leu | Gly 170 | Gly | Val | Lys | Val | Glu 175 | Arg | Gln | Val | Phe | Gly 180 |
| Glu | Ala | Thr | Lys | Gln 185 | Pro | Gly | Ile | Thr | Phe 190 | Ile | Ala | Ala | Lys | Phe 195 |
| Asp | Gly | Ile | Leu | Gly 200 | Met | Ala | Tyr | Pro | Arg 205 | Ile | Ser | Val | Asn | Asn 210 |
| Val | Leu | Pro | Val | Phe 215 | Asp | Asn | Leu | Met | Gln 220 | Gln | Lys | Leu | Val | Asp 225 |
| Gln | Asn | Ile | Phe | Ser 230 | Phe | Tyr | Leu | Ser | Arg 235 | Asp | Pro | Asp | Ala | Gln 240 |
| Pro | Gly | Gly | Glu | Leu 245 | Met | Leu | Gly | Gly | Thr 250 | Asp | Ser | Lys | Tyr | Tyr 255 |
| Lys | Gly | Ser | Leu | Ser 260 | Tyr | Leu | Asn | Val | Thr 265 | Arg | Lys | Ala | Tyr | Trp 270 |
| Gln | Val | His | Leu | Asp 275 | Gln | Val | Glu | Val | Ala 280 | Ser | Gly | Leu | Thr | Leu 285 |
| Cys | Lys | Glu | Gly | Cys 290 | Glu | Ala | Ile | Val | Asp 295 | Thr | Gly | Thr | Ser | Leu 300 |
| Met | Val | Gly | Pro | Val 305 | Asp | Glu | Val | Arg | Glu 310 | Leu | Gln | Lys | Ala | Ile 315 |
| Gly | Ala | Val | Pro | Leu 320 | Ile | Gln | Gly | Glu | Tyr 325 | Met | Ile | Pro | Cys | Glu 330 |
| Lys | Val | Ser | Thr | Leu 335 | Pro | Ala | Ile | Thr | Leu 340 | Lys | Leu | Gly | Gly | Lys 345 |
| Gly | Tyr | Lys | Leu | Ser 350 | Pro | Glu | Asp | Tyr | Thr 355 | Leu | Lys | Val | Ser | Gln 360 |
| Ala | Gly | Lys | Thr | Leu 365 | Cys | Leu | Ser | Gly | Phe 370 | Met | Gly | Met | Asp | Ile 375 |
| Pro | Pro | Pro | Ser | Gly 380 | Pro | Leu | Trp | Ile | Leu 385 | Gly | Asp | Val | Phe | Ile 390 |
| Gly | Arg | Tyr | Tyr | Thr 395 | Val | Phe | Asp | Arg | Asp 400 | Asn | Asn | Arg | Val | Gly 405 |
| Phe | Ala | Glu | Ala | Ala 410 | Arg | Leu | | | | | | | | |

( 2 ) INFORMATION FOR SEQ ID NO:13:

( i ) SEQUENCE CHARACTERISTICS:
        ( A ) LENGTH: 396 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:13:

```
Met Lys Thr Leu Leu Leu Leu Leu Leu Val Leu Leu Glu Leu Gly
                 5                  10                  15
Glu Ala Gln Gly Ser Leu His Arg Val Pro Leu Arg Arg His Pro
                20                  25                  30
Ser Leu Lys Lys Lys Leu Arg Ala Arg Ser Gln Leu Ser Glu Phe
                35                  40                  45
Trp Lys Ser His Asn Leu Asp Met Ile Gln Phe Thr Glu Ser Cys
                50                  55                  60
Ser Met Asp Gln Ser Ala Lys Glu Pro Leu Ile Asn Tyr Leu Asp
                65                  70                  75
Met Glu Tyr Phe Gly Thr Ile Ser Ile Gly Ser Pro Pro Gln Asn
                80                  85                  90
Phe Thr Val Ile Phe Asp Thr Gly Ser Ser Asn Leu Trp Val Pro
                95                  100                 105
Ser Val Tyr Cys Thr Ser Pro Ala Cys Lys Thr His Ser Arg Phe
                110                 115                 120
Gln Pro Ser Gln Ser Ser Thr Tyr Ser Gln Pro Gly Gln Ser Phe
                125                 130                 135
Ser Ile Gln Tyr Gly Thr Gly Ser Leu Ser Gly Ile Ile Gly Ala
                140                 145                 150
Asp Gln Val Ser Val Glu Gly Leu Thr Val Val Gly Gln Gln Phe
                155                 160                 165
Gly Glu Ser Val Thr Glu Pro Gly Gln Thr Phe Val Asp Ala Glu
                170                 175                 180
Phe Asp Gly Ile Leu Gly Leu Gly Tyr Pro Ser Leu Ala Val Gly
                185                 190                 195
Gly Val Thr Pro Val Phe Asp Asn Met Met Ala Gln Asn Leu Val
                200                 205                 210
Asp Leu Pro Met Phe Ser Val Tyr Met Ser Ser Asn Pro Glu Gly
                215                 220                 225
Gly Ala Gly Ser Glu Leu Ile Phe Gly Gly Tyr Asp His Ser His
                230                 235                 240
Phe Ser Gly Ser Leu Asn Trp Val Pro Val Thr Lys Gln Ala Tyr
                245                 250                 255
Trp Gln Ile Ala Leu Asp Asn Ile Gln Val Gly Gly Thr Val Met
                260                 265                 270
Phe Cys Ser Glu Gly Cys Gln Ala Ile Val Asp Thr Gly Thr Ser
                275                 280                 285
Leu Ile Thr Gly Pro Ser Asp Lys Ile Lys Gln Leu Gln Asn Ala
                290                 295                 300
Ile Gly Ala Ala Pro Val Asp Gly Glu Tyr Ala Val Glu Cys Ala
                305                 310                 315
Asn Leu Asn Val Met Pro Asp Val Thr Phe Thr Ile Asn Gly Val
                320                 325                 330
Pro Tyr Thr Leu Ser Pro Thr Ala Tyr Thr Leu Leu Asp Phe Val
                335                 340                 345
```

| | | | | | | | | | | | | |
|---|---|---|---|---|---|---|---|---|---|---|---|---|
| Asp | Gly | Met | Gln | Phe<br>350 | Cys | Ser | Ser | Gly | Phe<br>355 | Gln | Gly | Leu | Asp | Ile<br>360 |
| His | Pro | Pro | Ala | Gly<br>365 | Pro | Leu | Trp | Ile | Leu<br>370 | Gly | Asp | Val | Phe | Ile<br>375 |
| Arg | Gln | Phe | Tyr | Ser<br>380 | Val | Phe | Asp | Arg | Gly<br>385 | Asn | Asn | Arg | Val | Gly<br>390 |
| Leu | Ala | Pro | Ala | Val<br>395 | Pro | | | | | | | | | |

( 2 ) INFORMATION FOR SEQ ID NO:14:

( i ) SEQUENCE CHARACTERISTICS:
        ( A ) LENGTH: 255 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:14:

| | | | | | | | | | | | | | |
|---|---|---|---|---|---|---|---|---|---|---|---|---|---|
| Met | Gln | Pro | Leu | Leu<br>5 | Leu | Leu | Leu | Ala | Phe<br>10 | Leu | Leu | Pro | Thr | Gly<br>15 |
| Ala | Glu | Ala | Gly | Glu<br>20 | Ile | Ile | Gly | Gly | Arg<br>25 | Glu | Ser | Arg | Pro | His<br>30 |
| Ser | Arg | Pro | Tyr | Met<br>35 | Ala | Tyr | Leu | Gln | Ile<br>40 | Gln | Ser | Pro | Ala | Gly<br>45 |
| Gln | Ser | Arg | Cys | Gly<br>50 | Gly | Phe | Leu | Val | Arg<br>55 | Glu | Asp | Phe | Val | Leu<br>60 |
| Thr | Ala | Ala | His | Cys<br>65 | Trp | Gly | Ser | Asn | Ile<br>70 | Asn | Val | Thr | Leu | Gly<br>75 |
| Ala | His | Asn | Ile | Gln<br>80 | Arg | Arg | Glu | Asn | Thr<br>85 | Gln | Gln | His | Ile | Thr<br>90 |
| Ala | Arg | Arg | Ala | Ile<br>95 | Arg | His | Pro | Gln | Tyr<br>100 | Asn | Gln | Arg | Thr | Ile<br>105 |
| Gln | Asn | Asp | Ile | Met<br>110 | Leu | Leu | Gln | Leu | Ser<br>115 | Arg | Arg | Val | Arg | Arg<br>120 |
| Asn | Arg | Asn | Val | Asn<br>125 | Pro | Val | Ala | Leu | Pro<br>130 | Arg | Ala | Gln | Glu | Gly<br>135 |
| Leu | Arg | Pro | Gly | Thr<br>140 | Leu | Cys | Thr | Val | Ala<br>145 | Gly | Trp | Gly | Arg | Val<br>150 |
| Ser | Met | Arg | Arg | Gly<br>155 | Thr | Asp | Thr | Leu | Arg<br>160 | Glu | Val | Gln | Leu | Arg<br>165 |
| Val | Gln | Arg | Asp | Arg<br>170 | Gln | Cys | Leu | Arg | Ile<br>175 | Phe | Gly | Ser | Tyr | Asp<br>180 |
| Pro | Arg | Arg | Gln | Ile<br>185 | Cys | Val | Gly | Asp | Arg<br>190 | Arg | Glu | Arg | Lys | Ala<br>195 |
| Ala | Phe | Lys | Gly | Asp<br>200 | Ser | Gly | Gly | Pro | Leu<br>205 | Leu | Cys | Asn | Asn | Val<br>210 |
| Ala | His | Gly | Ile | Val<br>215 | Ser | Tyr | Gly | Lys | Ser<br>220 | Ser | Gly | Val | Pro | Pro<br>225 |
| Glu | Val | Phe | Thr | Arg<br>230 | Val | Ser | Ser | Phe | Leu<br>235 | Pro | Trp | Ile | Arg | Thr<br>240 |
| Thr | Met | Arg | Ser | Phe<br>245 | Lys | Leu | Leu | Asp | Gln<br>250 | Met | Glu | Thr | Pro | Leu<br>255 |

What is claimed is:

1. An isolated polynucleotide comprising a member selected from the group consisting of:

(a) a polynucleotide encoding the polypeptide comprising amino acid 1 to amino acid 214 as set forth in SEQ ID NO:2; and (b) a polynucleotide which hybridizes to and which is at least 95% complementary to the polynucleotide of (a).

2. The polynucleotide of claim 1 wherein said member is (a).

3. The polynucleotide of claim 1 wherein said member is (b).

4. The polynucleotide of claim 2 wherein said member encodes a polypeptide comprising amino acid −115 to amino acid 214 of SEQ ID NO:2.

5. The polynucleotide of claim 2 wherein said member encodes a polypeptide comprising amino acid −100 to amino acid 214 as set forth in SEQ ID NO:2.

6. An isolated polynucleotide comprising a polynucleotide which hybridizes to and which is at least 95% complementary to the polynucleotide of claim 4.

7. An isolated polynucleotide comprising a polynucleotide which hybridizes to and which is at least 95% complementary to the polynucleotide of claim 5.

8. The polynucleotide of claim 1 wherein said member comprises nucleotide 1 to nucleotide 1619 of SEQ ID NO:1.

9. The polynucleotide of claim 1 wherein said member comprises nucleotide 20 to nucleotide 1006 of SEQ ID NO:1.

10. The polynucleotide of claim 1 wherein said member comprises nucleotide 65 to nucleotide 1006 of SEQ ID NO:1.

11. An isolated polynucleotide comprising:

a polynucleotide which hybridizes to and which is at least 95% complementary to the polynucleotide of claim 10.

12. The polynucleotide of claim 1 wherein said member comprises nucleotide 305 to nucleotide 1006 of SEQ ID NO:1.

13. The polynucleotide of claim 1 wherein the polynucleotide is DNA.

14. The polynucleotide of claim 2 wherein the polynucleotide is DNA.

15. The polynucleotide of claim 4 wherein the polynucleotide is DNA.

16. The polynucleotide of claim 5 wherein the polynucleotide is DNA.

17. The polynucleotide of claim 2 wherein the polynucleotide is RNA.

18. An isolated polynucleotide comprising a member selected from the group consisting of:

(a) a polynucleotide encoding a mature polypeptide encoded by the cathepsin polynucleotide contained in ATCC Deposit No, 75671; and (b) a polynucleotide which hybridizes to and which is at least 95% complementary to the polynucleotide of (a).

19. The polynucleotide of claim 18 wherein said member is (a).

20. The polynucleotide of claim 18 wherein said member is (b).

21. The polynucleotide of claim 18 wherein the polynucleotide is DNA.

22. The polynucleotide of claim 18 wherein said member comprises the cathepsin O polynucleotide contained in ATCC Deposit No, 75671, which encodes for the mature polypeptide.

23. The polynucleotide of claim 19 wherein said member comprises:

cathepsin O polynucleotide contained in ATCC Deposit No. 75671.

24. An isolated polynucleotide comprising a polynucleotide which hybridizes to and which is 95% complementary to the polynucleotide of claim 23.

25. The polynucleotide of claim 24 wherein said polynucleotide comprises the cathepsin O polynucleotide contained in ATCC Deposit No. 75671.

26. A vector containing the polynucleotide of claim 2 wherein said polynucleotide is DNA.

27. A vector containing the polynucleotide of claim 4 wherein said polynucleotide is DNA.

28. A vector containing the polynucleotide of claim 5 wherein said polynucleotide is DNA.

29. A vector containing the polynucleotide of claim 9 wherein said polynucleotide is DNA.

30. A vector containing the polynucleotide of claim 10 wherein said polynucleotide is DNA.

31. A vector containing the polynucleotide of claim 12 wherein said polynucleotide is DNA.

32. A vector containing the polynucleotide of claim 19 wherein said polynucleotide is DNA.

33. A host cell transformed or transfected with the vector of claim 26.

34. A host cell transformed or transfected with the vector of claim 27.

35. A host cell transformed or transfected with the vector of claim 28.

36. A host cell transformed or transfected with the vector of claim 29.

37. A host cell transformed or transfected with the vector of claim 30.

38. A host cell transformed or transfected with the vector of claim 31.

39. A host cell transformed or transfected with the vector of claim 32.

* * * * *